United States Patent
Edelbrock

(10) Patent No.: US 8,083,884 B2
(45) Date of Patent: Dec. 27, 2011

(54) METHOD OF FORMING A MULTILAYER TEST SENSOR

(75) Inventor: Andrew J. Edelbrock, Granger, IN (US)

(73) Assignee: Bayer Healthcare LLC, Tarrytown, NY (US)

( * ) Notice: Subject to any disclaimer, the term of this patent is extended or adjusted under 35 U.S.C. 154(b) by 526 days.

(21) Appl. No.: 12/086,240

(22) PCT Filed: Dec. 21, 2006

(86) PCT No.: PCT/US2006/048872
§ 371 (c)(1),
(2), (4) Date: Jun. 9, 2008

(87) PCT Pub. No.: WO2007/075935
PCT Pub. Date: Jul. 5, 2007

(65) Prior Publication Data
US 2009/0159197 A1    Jun. 25, 2009

Related U.S. Application Data

(60) Provisional application No. 60/754,141, filed on Dec. 27, 2005.

(51) Int. Cl.
*B32B 38/00* (2006.01)
*B32B 38/10* (2006.01)

(52) U.S. Cl. ........ 156/257; 156/250; 156/252; 156/253; 156/256; 204/403.03; 204/403.12; 204/403.14

(58) Field of Classification Search ........... 156/250, 156/252, 253, 256; 204/403.3, 403.12, 403.14
See application file for complete search history.

(56) References Cited

U.S. PATENT DOCUMENTS

| 4,549,454 A | * | 10/1985 | Yamashita | ............. 83/27 |
| 6,531,040 B2 | | 3/2003 | Musho et al. | ............. 204/401 |
| 6,662,439 B1 | | 12/2003 | Bhullar | ............. 29/825 |
| 2005/0016846 A1 | | 1/2005 | Groll et al. | ............. 204/403.03 |
| 2005/0123443 A1 | | 6/2005 | Fujiwara et al. | ............. 422/58 |

FOREIGN PATENT DOCUMENTS
WO    WO 03/012422 A1    2/2003

OTHER PUBLICATIONS

Written Opinion corresponding to International Patent Application No. PCT/US2006/048872, European Patent Office, dated Jun. 22, 2007, 5 pages.
International Search Report corresponding to International Patent Application No. PCT/US2006/048872, European Patent Office, dated Jun. 22, 2007, 3 pages.

* cited by examiner

*Primary Examiner* — Mark A Osele
*Assistant Examiner* — Christopher C Caillouet
(74) *Attorney, Agent, or Firm* — Nixon Peabody LLP

(57) ABSTRACT

A method of forming an electrochemical multilayer test sensor that includes a base, a second layer and a reactive layer. The reactive area includes an enzyme. The test sensor is adapted to be used in a meter and assist in determining the concentration of an analyte. A plurality of electrodes and their respective conductive leads are partially defined on the base. After partially defining the plurality of electrodes and their respective conductive leads on the base, the base is attached to a second layer to define a reaction zone in which the plurality of electrodes are fully defined. After attaching the base to the second layer, the plurality of conductive leads on the base of the test sensor are fully defined.

20 Claims, 11 Drawing Sheets

METHOD OF FORMING A MULTILAYER TEST SENSOR

CROSS-REFERENCE TO RELATED APPLICATIONS

This application claims priority to Application No. 60/754,141 filed on Dec. 27, 2005, which is incorporated by reference in its entirety.

FIELD OF THE INVENTION

The present invention generally relates to a method of forming a test sensor. More specifically, the present invention generally relates to a method of forming a multilayer test sensor that is adapted to assist in determining a concentration of an analyte.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with blood glucose. One type of test sensor is a multi-layer test sensor that includes a base and a lid. The base has been attached to the lid in the multi-layer test sensor. One method of attaching the base to the lid is lamination. The act of laminating the base and the lid often has high, less desirable tolerances. In other words, the laminating of the base and the lid tends to have variances that are less than desirable (i.e., +/−0.015 in.). When the lamination of the base and the lid is not properly aligned, the base and the lid are said to be misregistered.

An example of a misregistered base and lid is shown in prior art FIGS. 1a-c. FIG. 1a depicts a sensor-ribbon strip 10 that includes a base-ribbon strip 20 and a lid-ribbon strip 30. The base-ribbon strip 20 includes a plurality of laser cuts 22a-c that defines a plurality of conductive leads or traces 26a-d thereon. The conductive leads or traces are the lead portions of the electrodes. To better show the laser cuts 22a-c formed on the base-ribbon strip 20, the laser cuts 22a-c have been shown extending upwardly above respective apertures 28 formed in the lid-ribbon strip 30 even though they would be partially hidden by the lid-ribbon strip 30. Additionally, FIGS. 1a-c highlight only the areas that will form a portion of the conductive leads or traces, while the actual cuts to form the electrodes or other features of the test sensor are not depicted.

The lid-ribbon strip 30 of FIG. 1a forms a plurality of registration apertures 32a,b. The lid-ribbon strip 30 is laminated to the base-ribbon strip 20. As shown in FIG. 1a, the lamination of the lid-ribbon strip 30 and the base-ribbon strip 20 is not properly aligned (i.e., misregistered). The misregistration of the lid-ribbon strip 30 and the base-ribbon strip 20 of FIG. 1a results in conductive leads 26a-d being of unequal widths. Thus, the plurality of test sensors formed from the sensor-ribbon strip 10 would have conductive leads 26a-d of unequal widths.

When the base and the lid are misregistered, conductive problems between the conductive leads of the test sensor and the meter or instrument may result. For example, misregistration may result in a short between the conductive leads of the test sensors and contacts of the instrument. If a short occurs, the instrument produces an erroneous reading of an analyte concentration or does not produce any reading of the analyte concentration. Misregistration may also result in an erroneous reading of an analyte concentration because the areas of the conductive leads are incorrect.

Therefore, it would be desirable to use a method that eliminates the lamination tolerances of the base and the lid.

SUMMARY OF THE INVENTION

According to one method, an electrochemical multilayer test sensor is formed that includes a base, a second layer and a reactive layer. The reactive area includes an enzyme. The test sensor is adapted to be used in a meter and assist in determining the concentration of an analyte. A plurality of electrodes and their respective conductive leads are partially defined on the base. After partially defining the plurality of electrodes and their respective conductive leads on the base, the base is attached to a second layer to define a reaction zone in which the plurality of electrodes are fully defined. After attaching the base to the second layer, the plurality of conductive leads on the base of the test sensor are fully defined.

According to another method, an electrochemical multi-layer test sensor is formed that includes a base, a second layer and a reactive layer. The reactive area includes an enzyme. The test sensor is adapted to be used in a meter and assist in determining the concentration of an analyte. A plurality of electrodes and their respective conductive leads on the base are partially defined via a laser. After partially defining the plurality of electrodes and their respective conductive leads on the base, the base is attached to a second layer to define a reaction zone in which the plurality of electrodes are fully defined. After attaching the base to the second layer, the plurality of conductive leads on the base of the test sensor are fully defined. The test sensor is excised from the attached base and the second layer.

BRIEF DESCRIPTION OF THE DRAWINGS

FIG. 1b is a cross-sectional view taken generally along lines 1b-1b of prior art FIG. 1a.

FIG. 1c is a cross-sectional view taken generally along lines 1c-1c of prior art FIG. 1a.

FIG. 4b is a cross-sectional view taken generally along lines 4b-4b of FIG. 4a.

FIG. 4c is a cross-sectional view taken generally along lines 4c-4c of FIG. 4a.

FIG. 7b is a cross-sectional view taken generally along lines 7b-7b of FIG. 7a.

DETAILED DESCRIPTION OF ILLUSTRATED EMBODIMENTS

The present invention is directed to an improved method of forming a multilayer test sensor by eliminating or reducing problems between the conductive leads or traces and the contacts of the instrument caused by misregistering the base and the lid in the attachment (e.g., lamination) act. By eliminating or reducing such problems, erroneous readings of an analyte concentration are reduced, as well as no readings of an analyte concentration are reduced.

In one embodiment, a test sensor is adapted to receive a fluid sample and is analyzed using an instrument or meter. The test sensor assists in determining the concentrations of analytes. Analytes that may be measured include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

The multilayer test sensors to be made using the inventive process include at least a base and a second layer such as a lid. The multilayer test sensors are electrochemical test sensors. The base and lid may be made from a variety of materials such as polymeric materials. Non-limiting examples of polymeric materials that may be used to form the base and lid include polycarbonate, polyethylene terephthalate (PET), polystyrene, polyimide, and combinations thereof. As will be discussed below, the multilayer test sensors may include additional layers such as a spacer. For example, a base, spacer and lid may form the multilayer test sensor in another embodiment.

Figure 2B:
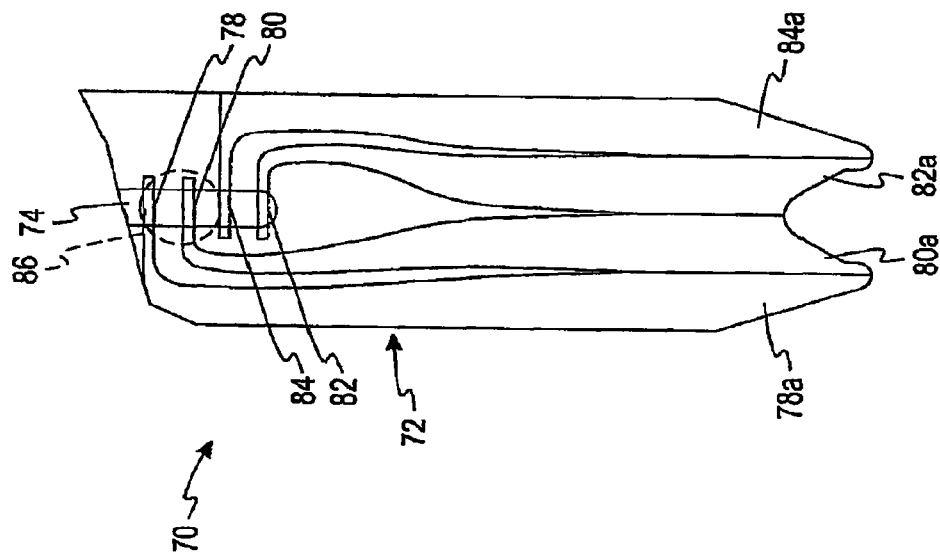
FIG. 2b is a top view of the test sensor of FIG. 2a without the lid.
Figure 2A:
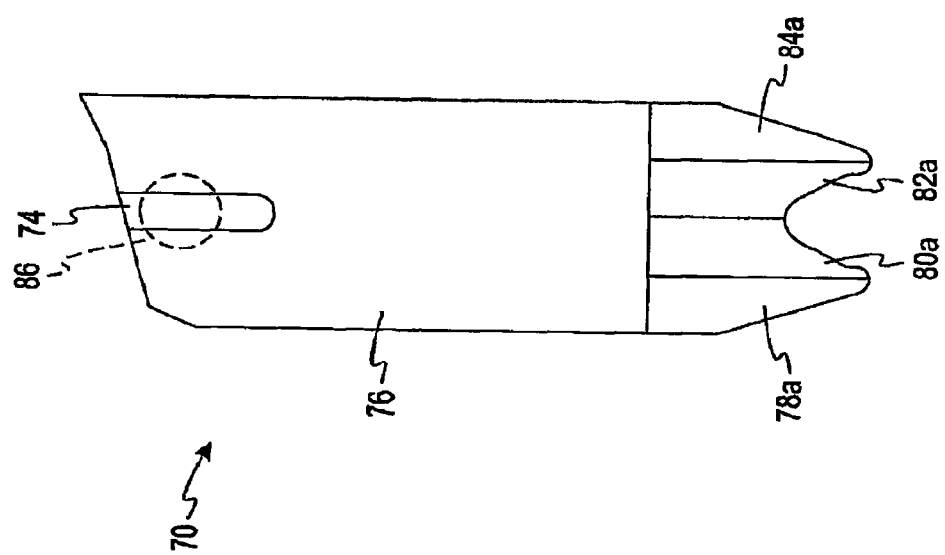
FIG. 2a is a top view of a test sensor including a lid according to one embodiment.

One non-limiting example of a test sensor is shown in FIGS. 2a, 2b. The test sensor may be formed from a sensor-ribbon strip that includes a base-ribbon strip and a lid-ribbon strip. FIGS. 2a, 2b depict a test sensor 70 that includes a base 72, capillary channel 74, a lid 76, a plurality of electrodes 78, 80, 82 and 84, and a plurality of conductive leads or traces 78a, 80a, 82a and 84a of the respective electrodes 78, 80, 82 and 84. The capillary channel 74 is formed when the base and the lid are attached to each other. The capillary channel 74 provides an enclosed flow path for introducing the sample into the test sensor 70 and eventually contacting the electrodes 78, 80, 82 and 84 and, thus, forms a reaction zone.

As shown in FIG. 2b, the test sensor 70 (without the lid 76) includes a reactive or fluid-receiving area 86 that contains an enzyme. The enzyme is selected to react with the desired analyte or analytes to be tested so as to assist in determining an analyte concentration of a fluid sample. The reactive area 86 includes a reagent for converting an analyte of interest (e.g., glucose) in a fluid test sample (e.g., blood) into a chemical species that is electrochemically measurable, in terms of the electrical current it produces, by the components of the electrode pattern. The reagent typically contains an enzyme (e.g., glucose oxidase), which reacts with the analyte (e.g., glucose) and with an electron acceptor (e.g., a ferricyanide salt) to produce an electrochemically measurable species that can be detected by the electrodes. The reactive area 86 may comprise a polymer, an enzyme, and an electron acceptor. The reactive area 86 also may include additional ingredients such as a buffer and a surfactant in some embodiments of the present invention. It is contemplated that other enzymes may be used to react with glucose such as glucose dehydrogenase. If the concentration of another analyte is to be determined, an appropriate enzyme is selected to react with the analyte.

The plurality of electrodes of FIG. 2b includes at least a counter electrode 78 and a working electrode 80 according to this embodiment. Other electrodes such as a detection electrode 82 and a hematocrit electrode 84 are shown in FIG. 2b. It is contemplated that more or less electrodes can be formed in the method of the present invention. For example, the test sensor may include exactly two electrodes or at least three electrodes. The exactly two electrodes may be a working electrode and a counter electrode in which an electrochemically created current flow when these electrodes are electrically connected and a potential is created between them.

The detection electrode may be an electrode that detects an underfill condition. It is contemplated that other electrodes may be used such as a hematocrit electrode that assists in correcting for the bias that occurs with selected hematocrit concentrations. Additional electrodes include, but are not limited to, electrodes that detect other analytes or species that may potentially interfere with the measurement of the desired analyte. Also, a second working electrode that assists in determining the concentration of another analyte may be used.

The electrodes are formed of conductive materials such as, for example, metallic materials (e.g., gold, platinum, palladium, rhodium, ruthenium, or combinations thereof) or carbon. Examples of components of electrochemical test sensors, including their operation, may be found at, for example, U.S. Pat. No. 6,531,040. It is contemplated that other components of electrochemical test sensors may be used other than that disclosed in, for example, U.S. Pat. No. 6,531,040.

The present invention is directed to an inventive process for forming a test sensor and, more specifically, an electrochemical test sensor. In one method, the electrochemical multilayer test sensors may be formed from a test-sensor ribbon. The ribbon is made from processes such as a multiple sheet process or a web process.

Figure 3:
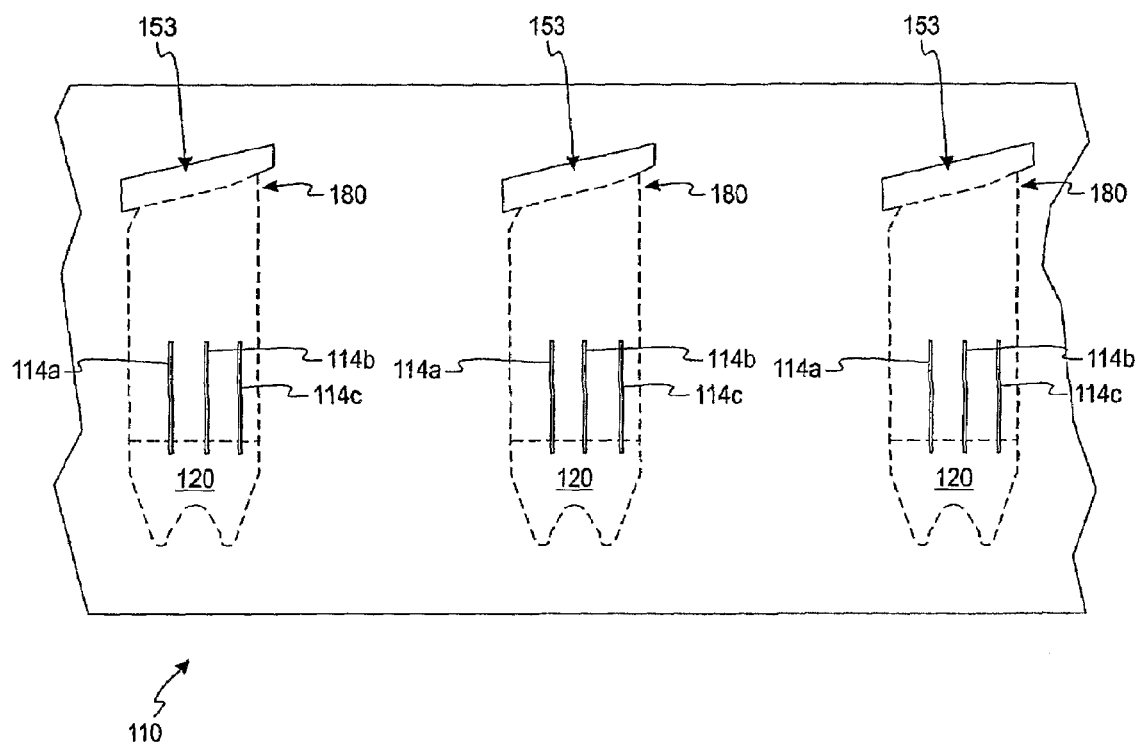
FIG. 3 is a top view of a base-ribbon strip according to one embodiment.

Referring to FIG. 3, a base-ribbon strip 110 is adapted to form a plurality of bases to be used in forming an electrochemical test sensor. The test sensors 180 to be formed from the base-ribbon strip 110 are depicted in FIG. 3 as dashed lines since they are not generally formed in the base-ribbon strip at this stage of processing. For improved efficiency, the test sensors are generally formed after the base-ribbon strip and the lid-ribbon strip have been attached.

The base-ribbon strip 110 of FIG. 3 is adapted to be attached (e.g., laminated) with a second layer such as, for example, a lid-ribbon strip. The base-ribbon strip 110 includes a conductive/reactive area 120, which will eventually form a plurality of conductive leads that is adapted to contact a meter or instrument. These conductive leads electrically connect the plurality of electrodes with the meter. The base-ribbon strip 110 also forms a plurality of apertures 153 that will assist in defining the test sensors. FIG. 3 depicts the areas that will form a portion of the conductive leads or traces in later processing, while the actual cuts to form the electrodes or other features of the test sensor are not depicted. Some of these features are depicted above in FIGS. 2a, 2b. It is contemplated that other patterns of electrodes may be used other than the pattern depicted in FIG. 2b. The electrodes, as well as other features, are typically formed on the base-ribbon strip at this stage of the processing.

Before attachment to the lid-ribbon strip, the base-ribbon strip 110 of FIG. 3, however, has not fully defined the plurality of conductive leads in the conductive area 120. In other words, the conductive leads of the plurality of electrodes are partially defined. In one process, a plurality of laser cuts 114a-c begins the process of defining the plurality of conductive leads in the conductive area 120. In this process, the plurality of electrodes has been partially defined but, as discussed above, are not shown in FIG. 3. The plurality of electrodes is not fully defined until the base-ribbon strip is attached to a second layer, which defines a reaction zone.

One process of defining the electrodes is by cutting the base-ribbon strip. For example, the plurality of electrodes may be defined by using a mask and a laser such as, for example, an Excimer laser or a carbon dioxide-based laser. One example of a mask is a chrome-on-glass mask in which the beam of light is only allowed to pass through selected areas.

According to another method, the plurality of electrodes on the base-ribbon strip 110 is partially formed with a laser using direct writing of the lines. As discussed above, the plurality of electrodes is not fully defined until the base-ribbon strip is attached to a second layer so as to define a reaction zone. In a method using a laser with direct writing of the lines, a laser beam of light is moved so as to partially define the plurality of electrodes. Lasers that produce a beam of energy capable of removing a layer and that can be moved to form a pattern may be used in this method. Non-limiting examples of such lasers are carbon dioxide-based lasers and yttrium-based lasers such as yttrium aluminum garnet (YAG) lasers.

It is contemplated that the plurality of electrodes may be defined on the base-ribbon strip by other methods such as, for example, printing (e.g., screen-printing), coating (e.g., reverse roll), vapor deposition, sputtering and electrochemical deposition.

Figure 4A:
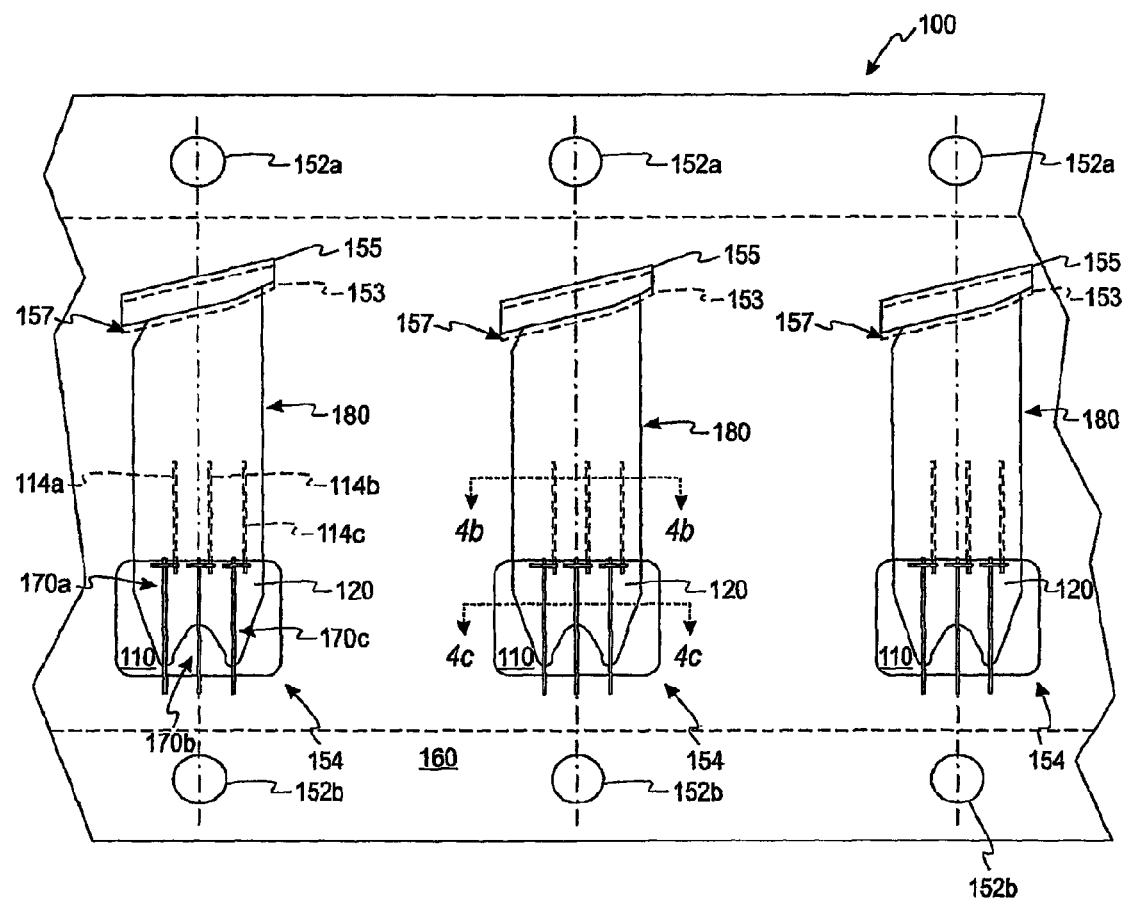
FIG. 4a is a top view of the base-ribbon strip of FIG. 3 laminated to a lid-ribbon strip according to one embodiment in which the base-ribbon strip and lid-ribbon strip are misregistered.
Figure 4B:
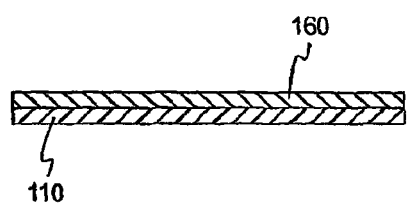
Figure 4C:
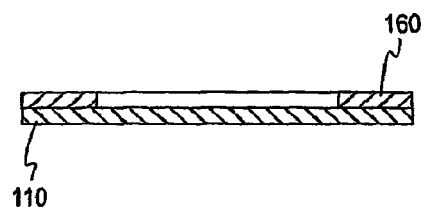
Figure 7A:
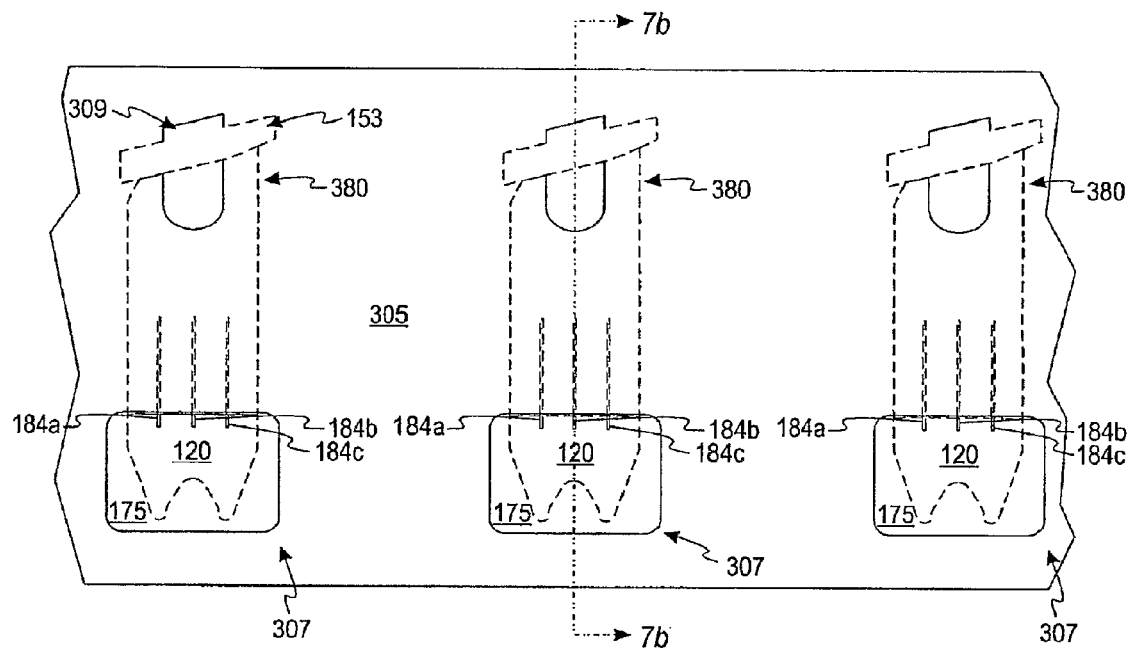
FIG. 7a is a top view of a spacer-ribbon strip overlying the base-ribbon strip of FIG. 5 according to a further embodiment.

After partially defining the plurality of electrodes, the base-ribbon strip 110 is attached to a second layer. In one embodiment, the base-ribbon strip 110 is attached to a lid-ribbon strip 160 to form a sensor-ribbon strip 100 such as shown in FIG. 4a. After attachment of the base-ribbon strip 110 and the lid-ribbon strip 160 so as to define a reaction zone, the plurality of electrodes is fully defined. It is contemplated that the second layer may be a spacer-ribbon strip such as shown in FIGS. 7-9. According to another embodiment, the second layer may be a spacer-lid ribbon strip combination in which the spacer-ribbon strip and lid-ribbon strip have been previously attached before the spacer-lid ribbon strip combination is later attached to the base-ribbon strip.

The base-ribbon strip (e.g., base-ribbon strip 110) may be attached to the second layer (e.g., lid-ribbon strip 160) using, for example, a pressure-sensitive adhesive and/or a hot melt adhesive. Thus, the attachment between the base-ribbon strip and the second surface uses pressure, heat or a combination thereof. It is contemplated that other materials may be used to attach the base-ribbon strip to the second surface. It is also contemplated that the base-ribbon strip and the lid-ribbon strip may be attached using ultrasonic energy or solvent welding.

As shown in FIG. 4a, the sensor-ribbon strip 100 includes the base-ribbon strip 110 and a lid-ribbon strip 160. The lid ribbon-strip 160 is adapted to form a plurality of lids. The lid ribbon-strip 160 forms a plurality of registration apertures 152a,b therein and also forms a plurality of apertures 154 adapted to allow access to respective conductive areas 120 of the base-ribbon strip 110. The conductive areas 120 are the areas in which the meter is adapted to contact the test sensors. The lid-ribbon strip 160 also forms a plurality of apertures 155 that assists in defining the periphery of the lid of the test sensor. In one embodiment, the plurality of apertures 155 and the plurality of apertures 153 are slightly offset, which allows for a slight overhang of the lid relative to the base in the test sensor. This is shown in FIG. 4a as offset area 157. The slight overhang assists in receiving and guiding the sample to the reactive or fluid-receiving area (not shown in FIG. 4a). It is contemplated that the test sensor may not include an overhang at the fluid-receiving area (i.e., neither the base nor the lid extends outwardly from the other at the fluid-receiving area).

Figure 4D:
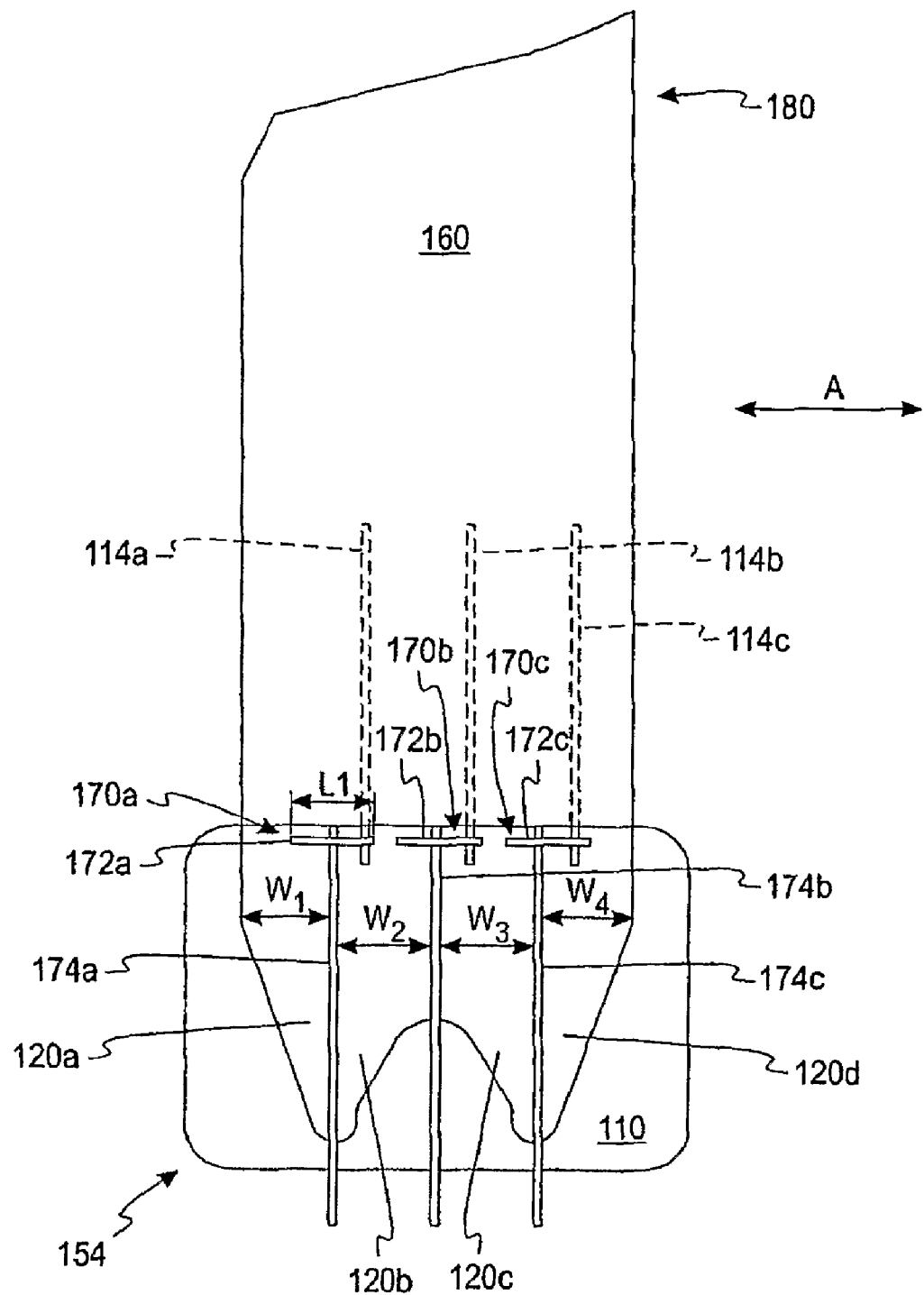
FIG. 4d is an enlarged top view of a portion of the base-ribbon strip of FIG. 3 and the lid-ribbon strip of FIG. 4a with a straight cut according to one embodiment.

As shown in FIGS. 4a, 4d, a plurality of laser cuts 170a-c fully defines the plurality of conductive leads 120a-d after the base-ribbon strip 110 and the lid-ribbon strip 160 have been laminated. The conductive leads 120a-d may be formed by the processes discussed above in connection with the plurality of electrodes, including laser processes. The laser cuts 170a-c and the laser cuts 114a-c are performed at distinct times and are considered to be separate acts. The laser used in forming the laser cuts 170a-c, however, may be the same laser used in the separate act of forming the laser cuts 114a-c. It is contemplated that the laser used in forming the laser cuts 170a-c and 114a-c may be different.

The plurality of laser cuts 170a-c gains assess to the conductive area 120 of the base-ribbon strip 110 through respective apertures 154 formed in the lid-ribbon strip 160. As shown in FIG. 4d, the plurality of laser cuts 170a-c is aligned such that the plurality of conductive leads 120a-d have generally the same widths W1-W4. Additionally, as best shown in FIG. 4d, a portion of the laser cuts 114a-c is exposed through the aperture 154.

Figure 1A:
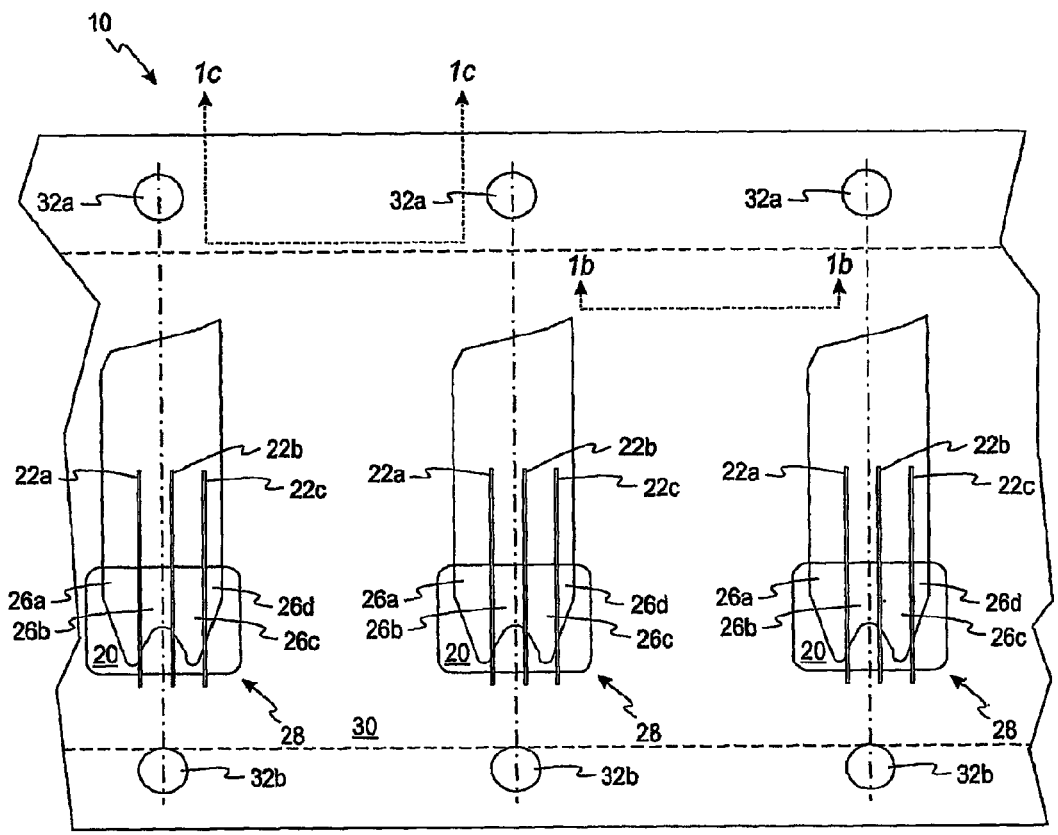
FIG. 1a is a top view of a prior art sensor-ribbon strip in which a base-ribbon strip and a lid-ribbon strip have been misregistered.
Figure 1B:
Figure 1C:
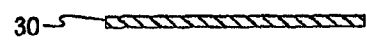

To prevent or inhibit the plurality of conductive leads 120a-d from being misregistered, the laser uses a guide or mark (registration apertures 152a,b in FIG. 4a). It is contemplated that other guides may be used to register the laser such as a plurality of marks formed from a laser-cutting operation on the base-ribbon strip. Laser-cutting is desirable because of the ability to maintain low manufacturing tolerances (typically less than 0.005 in.) when using mechanical or optical guides. By defining the conductive leads 120a-d using a laser and the same registration apertures used for excising the test sensors allows for tighter tolerances as compared to the prior art process discussed above in connection with prior art FIGS. 1a-1c.

As shown in FIGS. 4a, 4d, each of the plurality of laser cuts 170a-c is formed in a shape of a general "T". It is contemplated that the laser cuts may be of different shapes than depicted in FIGS. 4a, 4d. The laser cuts 170a-c of FIG. 4a have respective generally horizontal portions 172a-c and respective generally vertical portions 174a-c. The laser cuts 170a-c are formed so as to assist in physically connecting with respective plurality of cuts 114a-c.

The length (L1) of the generally horizontal portions 172a-c (shown in FIG. 4d) is selected to take into account the manufacturing variances of the respective cuts 114a-c. In other words, the greater the potential variance of the respective cuts 114a-c in the horizontal direction (directions of arrow A), the longer the length L1 of the generally horizontal portions 172a-c. Thus, respective laser cuts 114a-c desirably should not be misregistered to the left or the right of the respective generally horizontal portions 172a-c as viewed in FIGS. 4a, 4d. Additionally, to reduce the effect of manufacturing tolerances of the laser cuts 114a-c in the vertical direction (as viewed in FIGS. 4a, 4d), it is desirable for the laser cuts 114a-c to partially extend into the area accessible through apertures 154.

Figure 4E:
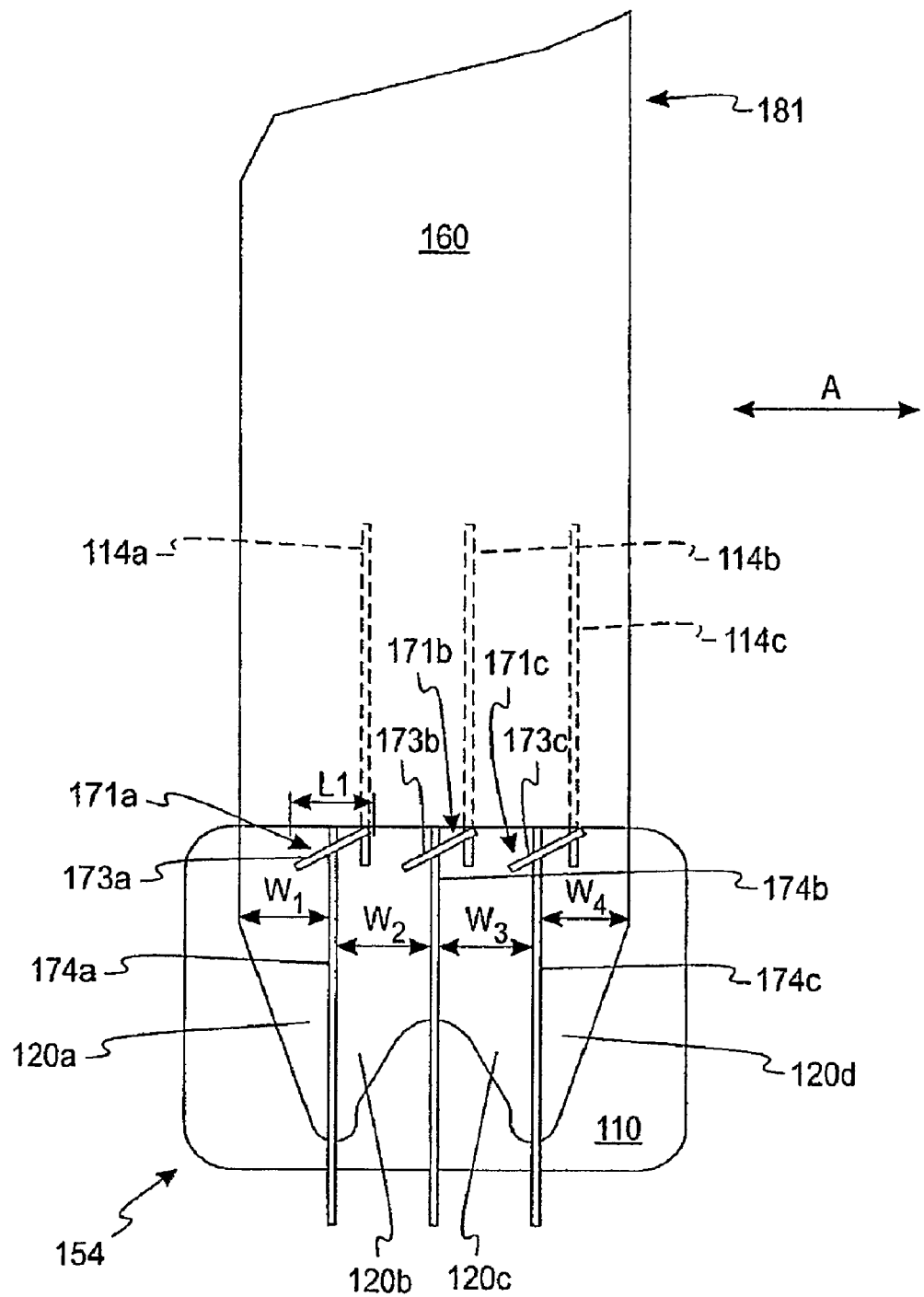
FIG. 4e is an enlarged top view of a portion of a base ribbon of FIG. 3 and a lid-ribbon strip of FIG. 4a with an angled cut according to one embodiment.

It is contemplated that the generally horizontal portions 172a-c of FIGS. 4a, 4d may be replaced by angled portions that physical connect with the plurality of cuts 114a-c. One non-limiting example is shown in FIG. 4e with laser cuts 171a-c including angular portions 173a-c. The angular portions 173a-c extend into and physically connect with the plurality of cuts 114a-c.

In one method, a mechanical punch is used to excise a plurality of test sensors in the sensor-ribbon strip (plurality of test sensors 180 in FIGS. 4a-4d and test sensor 181 in FIG. 4e). The mechanical punch extends through the base-ribbon strip 110 and the lid-ribbon strip 160. It is contemplated that the plurality of test sensors may be excised by other methods. In a desired embodiment, the registration apertures 152a,b of FIG. 4a assist in locating the mechanical punch that excises the test sensors from the sensor-ribbon strip 100.

Figure 5:
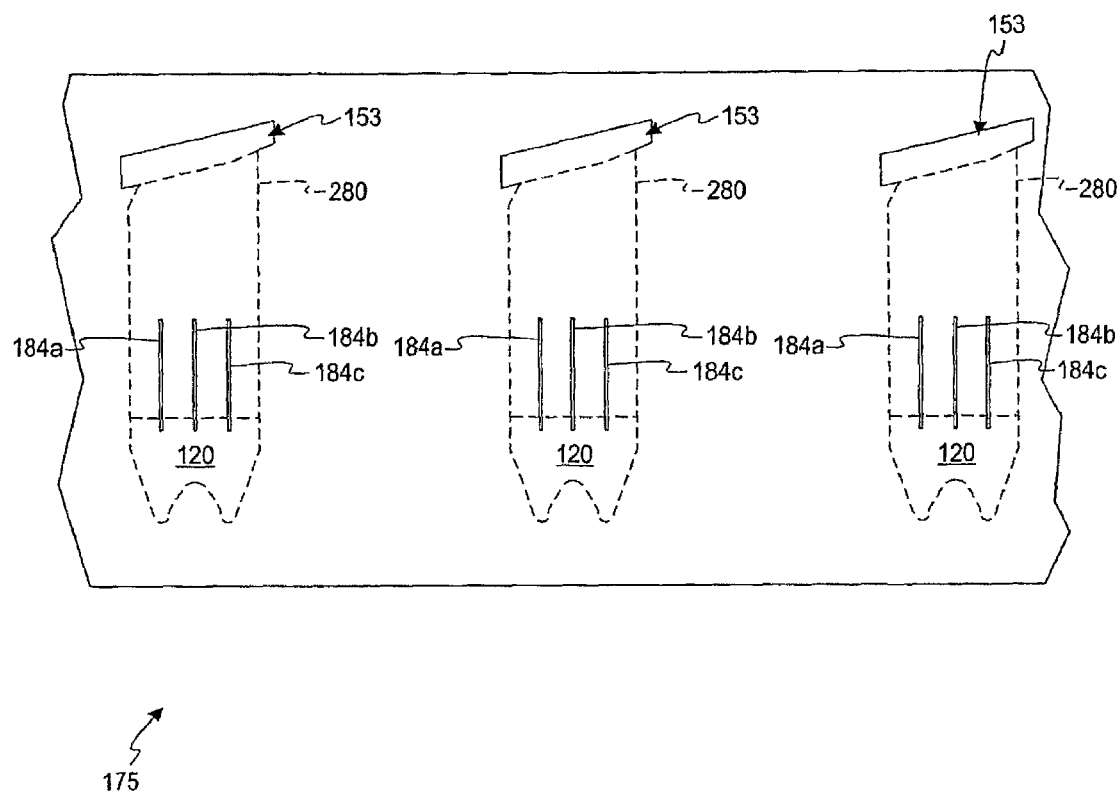
FIG. 5 is a top view of a base-ribbon strip according to another embodiment.
Figure 6:
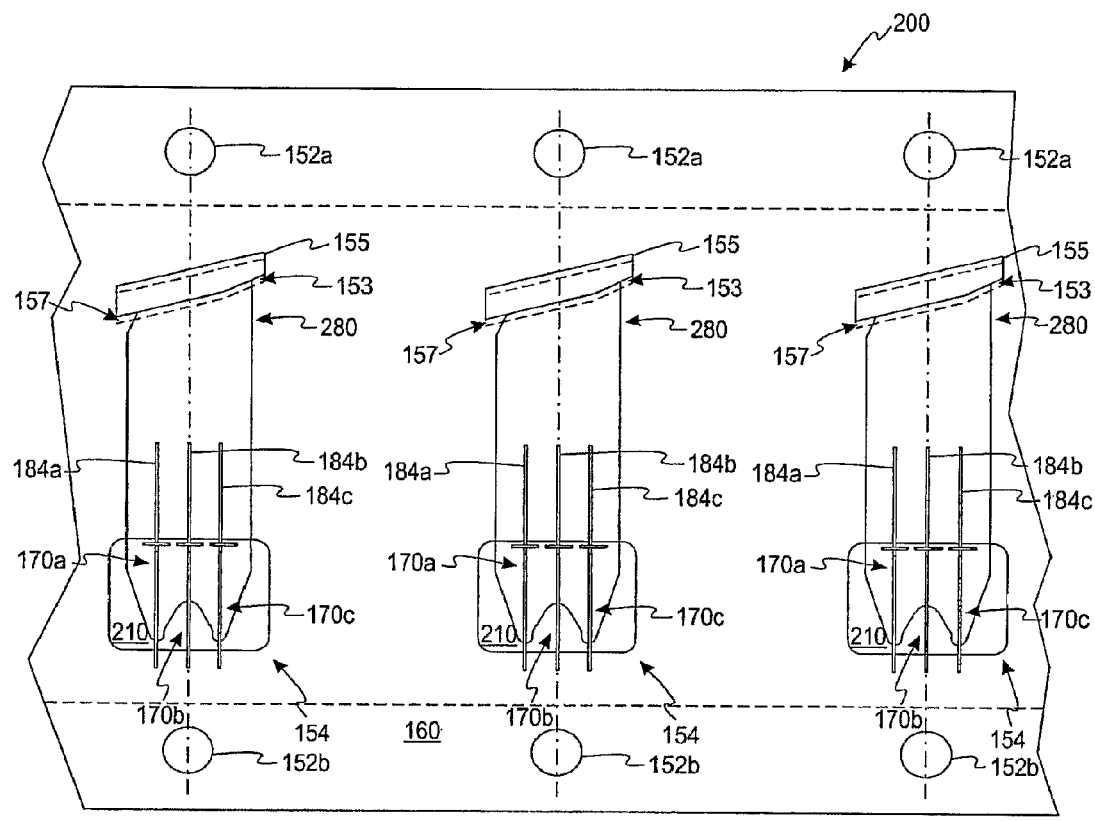
FIG. 6 is a top view of the base-ribbon strip of FIG. 5 laminated to a lid-ribbon strip in which the base-ribbon strip and the lid-ribbon strip are properly aligned according to another embodiment.

Referring to FIG. 6, a sensor-ribbon strip 200 includes base-ribbon strip 175 of FIG. 5 and the lid-ribbon strip 160 described above. The sensor-ribbon strip 200 of FIG. 6 forms a plurality of test sensors 280. The sensor-ribbon strip 200 of FIG. 6 is the same as the sensor-ribbon strip 100 of FIG. 4a except that the laser cuts 184a-c of FIGS. 5, 6 have been properly positioned, unlike the laser cuts 114a-c of FIGS. 3, 4a. The laser cuts 170a-c of the sensor-ribbon strip 200 of FIG. 6 are formed in the same location as the laser cuts 170a-c of the sensor-ribbon strip 100 of FIG. 4a even though the laser cuts 114a-c of FIGS. 4a,4d were misregistered and the laser cuts 184a-c of FIGS. 5,6 were properly registered. This is because the laser cuts 170a-c were formed using respective registration apertures 152a,b.

As discussed above, it is contemplated that the test sensor may include a spacer. In one embodiment depicted in FIGS. 7a, 7b, a base-ribbon strip 175 of FIG. 5 with a spacer-ribbon strip 305 attached thereto. The spacer-ribbon strip 305 includes a plurality of apertures 307 formed therein to allow access to the conductive areas 120 of the base-ribbon strip 175. It is contemplated that the apertures 307 may be shaped differently as long as the conductive areas 120 of the base-ribbon strip are accessible for later processing.

The spacer-ribbon strip 305 also forms a plurality of apertures 309. The apertures 309 of FIG. 7a are generally U-shaped such that the U-shape portion is open to provide a capillary space or fluid chamber between the base and the lid in the test sensor. It is contemplated that the aperture to form a capillary space or fluid chamber may be shaped differently than depicted in FIGS. 7a, 7b and 8.

Figure 7B:
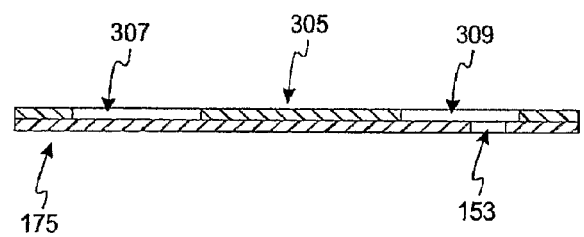
Figure 8:
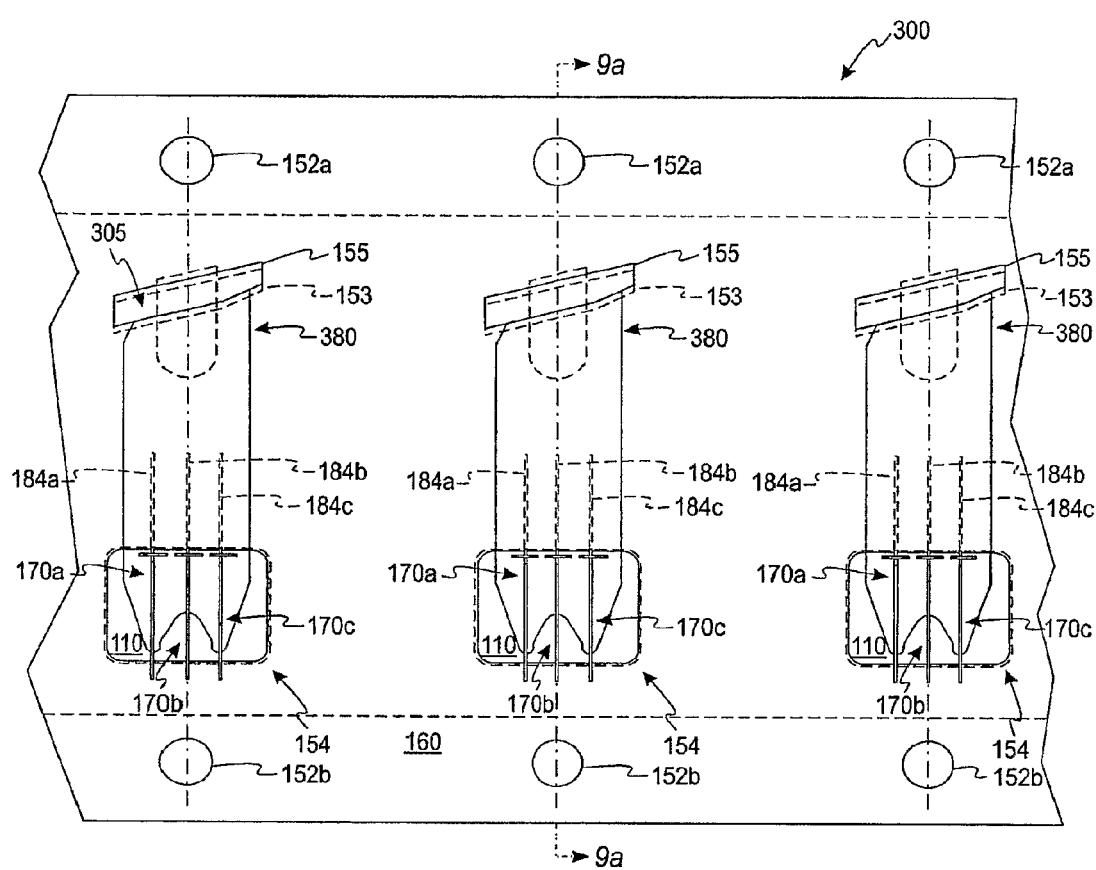
FIG. 8 is a top view of the base and spacer-ribbon strip of FIG. 7a laminated to a lid-ribbon strip in which the base-ribbon strip, spacer-ribbon strip and the lid-ribbon strip are properly aligned according to a further embodiment.
Figure 9A:
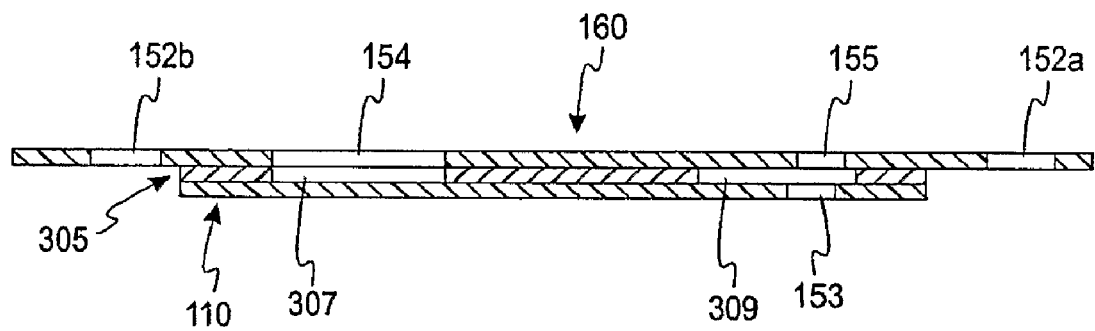
FIG. 9a is a cross-sectional view taken generally along lines 9a-9a of FIG. 8.
Figure 9B:
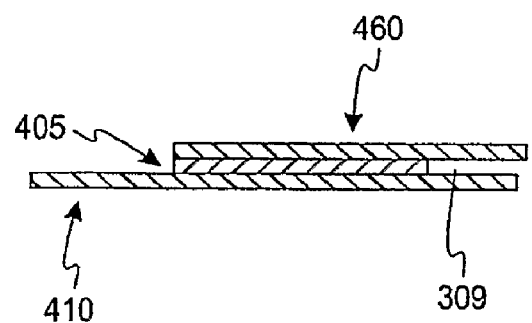
FIG. 9b is a cross-sectional view of a test sensor formed from the base/spacer/lid ribbon strip of FIG. 8 taken generally along lines 9a-9a of FIG. 8.

FIG. 8 depicts a sensor-ribbon strip 300 that includes the base-ribbon strip 175 and the spacer-ribbon strip 305 of FIGS. 7a, 7b and the lid-ribbon strip 160. The lid-sensor ribbon strip 160 is the same as described above in connection of FIG. 6. As shown in FIG. 8, only a small portion of the spacer-ribbon strip 305 is visible through the aperture 155 of the lid-ribbon strip 160. The cuts 170a-c are formed after the lid-ribbon strip 160, the spacer-ribbon strip 305 and the base-ribbon strip 175 are attached. As discussed above, the cuts 170a-c are formed in separate acts from the cuts 184a-c. It is contemplated that the spacer-ribbon strip may include the registration apertures instead of the lid-ribbon strip.

ALTERNATIVE PROCESS A

A method of forming an electrochemical multilayer test sensor, the multilayer test sensor including a base, a second layer and a reactive layer, the reactive area including an enzyme, the test sensor being adapted to be used in a meter and assist in determining the concentration of an analyte, the method comprising the acts of:

partially defining a plurality of electrodes and their respective conductive leads on the base;

after partially defining the plurality of electrodes and their respective conductive leads on the base, attaching the base to a second layer to define a reaction zone in which the plurality of electrodes are fully defined; and after attaching the base to the second layer, fully defining the plurality of conductive leads on the base of the test sensor.

ALTERNATIVE PROCESS B

The method of alternative process A wherein the plurality of conductive leads and plurality of electrodes are defined by a laser.

ALTERNATIVE PROCESS C

The method of alternative process A wherein the plurality of conductive leads and plurality of electrodes are defined by printing, coating, vapor deposition, sputtering or electrochemical deposition.

ALTERNATIVE PROCESS D

The method of alternative process A wherein the act of partially defining the plurality of electrodes includes using a laser.

ALTERNATIVE PROCESS E

The method of alternative process A wherein the second layer is a lid.

ALTERNATIVE PROCESS F

The method of alternative process A wherein the second layer is a spacer.

ALTERNATIVE PROCESS G

The method of alternative process A wherein the second layer is a spacer-lid combination.

ALTERNATIVE PROCESS H

The method of alternative process A wherein the second layer forms a plurality of guides.

ALTERNATIVE PROCESS I

The method of alternative process H wherein the plurality of guides is a plurality of registration apertures.

ALTERNATIVE PROCESS J

The method of alternative process A further including excising the multi-layer test sensor from the attached base and the second layer.

ALTERNATIVE PROCESS K

The method of alternative process J wherein the act of excising the multi-layer test sensor from the attached base and the second layer includes using a mechanical punch.

ALTERNATIVE PROCESS L

The method of alternative process J wherein the act of excising the multiple-test sensor and the act of defining the plurality of conductive traces are registered with each other.

ALTERNATIVE PROCESS M

The method of alternative process A wherein the base and the second layer are attached using an adhesive.

ALTERNATIVE PROCESS N

The method of alternative process A wherein the plurality of electrodes comprises a metallic conductive material.

ALTERNATIVE PROCESS O

The method of alternative process A wherein the enzyme is glucose oxidase or glucose dehydrogenase.

ALTERNATIVE PROCESS P

A method of forming an electrochemical multilayer test sensor, the multilayer test sensor including a base, a second layer and a reactive layer, the reactive area including an enzyme, the test sensor being adapted to be used in a meter and assist in determining the concentration of an analyte, the method comprising the acts of:

partially defining a plurality of electrodes and their respective conductive leads on the base via a laser;

after partially defining the plurality of electrodes and their respective conductive leads on the base, attaching the base to a second layer to define a reaction zone in which the plurality of electrodes are fully defined;

after attaching the base to the second layer, fully defining the plurality of conductive leads on the base of the test sensor; and excising the test sensor from the attached base and the second layer.

ALTERNATIVE PROCESS Q

The method of alternative process P wherein the second layer is a lid.

ALTERNATIVE PROCESS R

The method of alternative process P wherein the second layer is a spacer.

ALTERNATIVE PROCESS S

The method of alternative process P wherein the second layer is a spacer-lid combination.

ALTERNATIVE PROCESS T

The method of alternative process P wherein the act of excising the multi-layer test sensor from the attached base and the second layer includes using a mechanical punch.

ALTERNATIVE PROCESS U

The method of alternative process P wherein the act of excising the multiple-test sensor and the act of defining the plurality of conductive traces are registered with each other.

ALTERNATIVE PROCESS V

The method of alternative process P wherein the base and the second layer are attached using an adhesive.

ALTERNATIVE PROCESS W

The method of alternative process P wherein the plurality of electrodes comprises a metallic conductive material.

ALTERNATIVE PROCESS X

The method of alternative process P wherein the enzyme is glucose oxidase or glucose dehydrogenase.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention as defined by the appended claims.

The invention claimed is:

1. A method of forming an electrochemical multilayer test sensor, the multilayer test sensor including a base, a second layer and a reactive area, the reactive area including an enzyme, the test sensor being adapted to be used in a meter and assist in determining the concentration of an analyte, the method comprising the acts of:

partially defining a plurality of electrodes and their respective conductive leads on the base;

after partially defining the plurality of electrodes and their respective conductive leads on the base, attaching the base to a second layer to define a reaction zone in which the plurality of electrodes are fully defined, thereby leaving a portion of the base uncovered by the second layer; and after attaching the base to the second layer, further processing to define the plurality of conductive leads on the portion of the base which is uncovered by the second layer.

2. The method of claim 1, wherein the plurality of conductive leads and plurality of electrodes are defined by a laser.

3. The method of claim 1, wherein the plurality of conductive leads and plurality of electrodes are defined by printing, coating, vapor deposition, sputtering or electrochemical deposition.

4. The method of claim 1, wherein the act of partially defining the plurality of electrodes includes using a laser.

5. The method of claim 1, wherein the second layer is a lid.

6. The method of claim 1, wherein the second layer is a spacer.

7. The method of claim 1, wherein the second layer forms a plurality of guides.

8. The method of claim 1, further including excising the multi-layer test sensor from the attached base and the second layer.

9. The method of claim 8, wherein the act of excising the multi-layer test sensor from the attached base and the second layer includes using a mechanical punch.

10. The method of claim 8, wherein the act of excising the multiple-test sensor and the act of defining the plurality of conductive traces are registered with each other.

11. The method of claim 1, wherein the base and the second layer are attached using an adhesive.

12. The method of claim 1, wherein the plurality of electrodes comprises a metallic conductive material.

13. The method of claim 1, wherein the enzyme is glucose oxidase or glucose dehydrogenase.

14. A method of forming an electrochemical multilayer test sensor, the multilayer test sensor including a base, a second layer and a reactive area, the reactive area including an enzyme, the test sensor being adapted to be used in a meter and assist in determining the concentration of an analyte, the method comprising the acts of:

partially defining a plurality of electrodes and their respective conductive leads on the base via a laser;

after partially defining the plurality of electrodes and their respective conductive leads on the base, attaching the base to a second layer to define a reaction zone in which the plurality of electrodes are fully defined, thereby leaving a portion of the base uncovered by the second layer;

after attaching the base to the second layer, further processing to define the plurality of conductive leads on the portion of the base which is uncovered by the second layer; and excising the test sensor from the attached base and the second layer.

15. The method of claim 14, wherein the second layer is a lid.

16. The method of claim 14, wherein the second layer is a spacer.

17. The method of claim 14, wherein the act of excising the multi-layer test sensor from the attached base and the second layer includes using a mechanical punch.

18. The method of claim 14, wherein the act of excising the multiple-test sensor and the act of defining the plurality of conductive traces are registered with each other.

19. The method of claim 14, wherein the base and the second layer are attached using an adhesive.

20. The method of claim 14, wherein the enzyme is glucose oxidase or glucose dehydrogenase.

* * * * *